(12) United States Patent
Lott

(10) Patent No.: US 6,245,384 B1
(45) Date of Patent: Jun. 12, 2001

(54) PARTICLE COATING

(75) Inventor: Dennis L. Lott, Germantown, TN (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 0 days.

(21) Appl. No.: 08/375,456

(22) Filed: Jan. 19, 1995

Related U.S. Application Data

(63) Continuation-in-part of application No. 08/111,092, filed on Aug. 24, 1993, now abandoned.

(51) Int. Cl.$^7$ .................................................. B05D 7/00
(52) U.S. Cl. ..................... 427/220; 427/242; 427/384; 427/416
(58) Field of Search .................................. 427/212, 220, 427/242, 416, 384

(56) References Cited

U.S. PATENT DOCUMENTS

| | | | | |
|---|---|---|---|---|
| 3,438,797 | * | 4/1969 | Biddle | 424/476 |
| 4,021,262 | | 5/1977 | Guerrero et al. | . |
| 5,023,108 | | 6/1991 | Bagaria et al. | . |
| 5,389,129 | * | 2/1995 | Jordan | 106/10 |

* cited by examiner

*Primary Examiner*—Shrive Beck
*Assistant Examiner*—Bret B. Chen
(74) *Attorney, Agent, or Firm*—Robert A. Franks

(57) ABSTRACT

Particles such as tablets and gums which contain or are coated with sugar are provided with a wax coating, by spraying the particles with an aqueous-continuous emulsion having wax in the internal phase. The sprayed particles can be further coated with powdered wax and polished.

16 Claims, No Drawings

PARTICLE COATING

CROSS-REFERENCE TO RELATED APPLICATION

This is a continuation-in-part of application Ser. No. 08/111,092 filed on Aug. 24, 1993, now abandoned, the entire disclosure of which is incorporated herein by this reference.

INTRODUCTION TO THE INVENTION

The present invention relates to the coating of tabletted, pelletized or other particulate materials, and more particularly to providing a polished wax coating on such materials.

The usual wax coating processes for tablets or other particles intended for human consumption involve treating the particles with solutions of wax in volatile organic solvents, evaporating the solvents and tumbling the coated particles in a fabric-lined drum or pan to polish the wax. With many localities being quite sensitive to the potential for air pollution formed by reactions of hydrocarbons, halogenated hydrocarbons or other volatile solvents in the atmosphere, it has become unacceptable to discharge such vapors from an industrial facility. Many recovery systems for organic vapors are commercially available, but they are universally expensive to purchase, install and operate; of course, none of the systems operate with total efficiency, resulting in some emissions to the atmosphere and some degree of indoor pollution hazards to industrial workers.

The process further suffers from inefficiencies, in that it is necessary to apply the wax solution in one piece of equipment, such as a rotating pan, remove the particles for drying, then transfer the particles to the polishing equipment. Special facilities, such as an explosion-proof room, are frequently necessary for worker and equipment protection.

Another coating procedure involves tumbling particles in a pan having a fabric liner which is impregnated with a wax, or using a fabric-lined pan and tumbling with pieces of solid wax. In general, the resulting wax coatings are not sufficiently uniform, the coating process requires very long residence times and particles are subjected to undesirable impact forces (causing excessive particle breakage) from the prolonged tumbling. Sometimes, powdered wax is sprinkled over particles, then melted using heated air to consolidate the coating; this procedure also suffers from a lack of coating uniformity.

It would be highly desirable to apply the waxes in a fluid form which will not involve large amounts of volatile organic compounds, such as in an aqueous medium. It would further be desirable to avoid transferring particles to various pieces of equipment for the coating processing steps, while providing an attractive polished tablet or particle. Also, a process is desired which rapidly gives the desired wax coating.

U.S. Pat. No. 3,438,797 to Biddle teaches applying a sugar solution containing a small amount of a wax emulsion to pharmaceutical tablets which are sticky from the recent application of a sugar syrup coating. Upon drying, an unpolished coating is obtained, which can be imprinted with ink. It is stated that the ink will not adhere to polished wax coated tablets. A further application of a protective transparent wax coating and polishing are done after the imprinting, presumably using the above-described solvent-based process.

U.S. Pat. No. 4,021,262 to Guerrero et al. pertains to a transparent coating for fruits and vegetables which permits gas exchange but is a barrier to moisture. This coating is produced by applying an emulsion formed from Candelilla wax, an unstable soap and xylene or toluene. It does not appear that this produces a polished coating, and the emulsion does not totally avoid volatile organic solvents.

U.S. Pat. No. 5,023,108 to Bagaria et al. describes a coating process for pharmaceutical solids, involving the preparation of an emulsion from a wax/lipid, an emulsifying agent and water, spray drying the emulsion to form a powder, dispersing the powder in water, and coating the dispersion onto the surface of medicaments.

SUMMARY OF THE INVENTION

The present invention provides polished wax coated tablets or other particles by a method comprising spraying the particles with an aqueous-continuous emulsion containing a wax in a discontinuous phase, dusting the tablets or particles with a powdered wax and tumbling to polish. This method has been found useful for particles having a sugary or other surface having an affinity for water. When sugar-coated particles are to be provided with a polished coating, the method can be conducted in the same pans or other equipment used for applying the sugar coating, immediately following the sugar coating operation.

DETAILED DESCRIPTION OF THE INVENTION

In this discussion and the examples, all percentages are stated as percent by weight, unless otherwise specified.

Suitable particles for coating in the present invention include, without limitation, medicinal and other tablets, pills, granules, beads, caplets and pellets, as well as chewing gums, candies and the like. In general, the particles will have a large proportion of contained sugar or will have a sugar-based coating; methods for sugar coating are well known in the art and typically involve distributing a small amount of a concentrated aqueous solution (syrup) of sucrose onto particles contained in an inclined rotating pan, and blowing warm air onto the particles to hasten drying. Being manual and highly operator-dependent, many variations of sugar coating processes are known and the selection of a particular variation is not a matter of concern in the present invention. It is expected that those having skill in the art will experiment with their sugar coating processes to optimize the subsequent wax coating.

An example of the present method for applying a polished wax coating to particles includes the steps of:

(a) spraying a wax-containing emulsion of the oil-in-water type onto particles in a rotating pan;

(b) dusting a powdered wax over the particles; and (c) tumbling the coated particles in the pan to polish the wax.

Oil-in-water emulsions, also referred to in the art as "invert" emulsions, are characterized by a continuous aqueous phase having droplets of insoluble organic liquids dispersed throughout. While the emulsions of this invention may well comprise solid particles of wax dispersed in an aqueous medium upon cooling from the elevated temperatures at which the emulsions are formed, and thus are no longer true emulsions, they will be considered as being emulsions for purposes of the invention.

The emulsions are formed by mixing, under conditions of high shear, molten wax with water or an aqueous solution. To impart stability to the emulsion, one or more surface active agents also will be present at mixing; depending upon the nature of the surface active agents used, they can be dissolved or dispersed in either the aqueous material or the wax component, or can be separately introduced at the time of mixing. As is known in the art, various types of mixing are appropriate for emulsion formation, including forcing the two components together through a pump or vigorously agitating a mixture of the components in a vessel, under conditions of high shear. The method of emulsion formation is a matter of choice and is not critical to the invention.

Suitable waxes for use in the emulsions of the invention have melting points below about 100° C., so that they can be combined in liquid form with aqueous materials to form emulsions, without causing water to boil. The waxes can be of animal, plant or mineral origin, representative waxes including beeswax, candelilla wax, carnauba wax, rice wax, ceresin wax, montan wax, petroleum wax and the like.

Melting point is not a consideration for the powdered wax used as a final coating in certain embodiments of the invention, so the useful materials for this step can include any of the above waxes, plus synthetic hydrocarbon waxes. Mixtures of waxes can be used both for forming emulsions and in the final coating step.

In general, the formation of aqueous-continuous emulsions is facilitated by surface-active agents having hydrophilic-lipophilic balance values above about 9. This can be achieved with a single agent or a blend of agents having higher and lower values than the actual desired overall value for a given system. For example, Glyceryl monostearate (HLB about 11), Polysorbate 65 (a mixture of stearate esters of sorbitol and sorbitol anhydrides, mostly triesters, each mole being condensed with about 20 moles of ethylene oxide and the product having an HLB of 10.5) and Polysorbate 80 (a mixture of oleate esters of sorbitol and sorbitol anhydrides, mostly monoesters, each mole being condensed with about 20 moles of ethylene oxide and the product having an HLB of 15) are used together to form the emulsion of Example 1, infra. As is well known in the art of emulsification, some amount of experimentation is frequently required to establish the optimal surfactant or surfactant blend, the amount of surfactant and the emulsion-forming conditions for a given combination of ingredients; the design and conduct of such experimentation is well within the ordinary skill in the art.

In many instances, there will not be a need to ship or store the formed emulsions for long periods, their production being relatively uncomplicated and not requiring sophisticated equipment which is unavailable at the location of use. However, to prevent undesirable microbial growth, one or more biocides such as methylparaben or propylparaben will frequently be added. Of course, other biocides may be used, provided they are acceptable for ingestion at the levels present on coated particles and do not inhibit emulsion formation.

When a softer wax, such as beeswax, is used to form the emulsion, it frequently will be necessary to also coat the particles with a harder wax, such as carnauba wax, to obtain a very glossy polished finish. The preceding discussion has noted the technique of dusting powdered dry wax onto the emulsion-coated particles, then tumbling to polish the coating. It is also possible to incorporate the harder wax as a component of the emulsion, sometimes a useful practice when the particle to be coated has noticeable surface imperfections which would not be uniformly coated and polished by a powdered wax. While it is not desired to be bound to any particular theory, and the operation of the invention does not depend upon any theory, it is considered possible that the softer wax of the emulsion adheres firmly to the particle surface and provides a substrate to which the harder wax can form a strong bond.

In general, the final emulsions should have properties, such as viscosities, which are appropriate for the desired method of application to particles. In many instances it will be desired to apply the emulsions with spray equipment, so emulsions which are quite fluid are desired. Viscosity can be decreased by incorporating more water into the emulsion, either during its formation or subsequently with some emulsions, such as by water dilution just before use.

Viscosity is also affected by the wax content of the emulsion. It is generally desired to incorporate a maximum amount of wax, preferably at least six percent by weight; the maximum amount of wax will be dictated by the required fluidity of the emulsion, sprayable emulsions usually being obtained for wax concentrations up to about 20 percent by weight, depending upon the waxes chosen. Typically, the wax concentration will not exceed about fifteen percent.

As opposed to the teachings of the previously noted Biddle patent (U.S. Pat. No. 3,438,797), the present invention relates to emulsions which are substantially free of sugars. Sugars will undesirably increase the emulsion viscosity. The emulsions and procedure of the present invention produce polished wax coatings which can be imprinted with the usual inks; no further coating or polishing steps are needed to produce a finished particle.

It is an advantage of the invention that the entire coating and polishing operation can be conducted in a single rotating pan which does not normally require the addition of a fabric liner, and it is not necessary to remove particles from the pan for drying, etc. between the sugar coating, wax coating and polishing steps, until a final polished wax coating has been obtained. Particles emerge from the coating and polishing operation ready to be dried, if necessary, imprinted, if desired, and packaged.

The invention will be further described in the following examples, which are not intended to be limiting, the invention being fully defined solely by the appended claims.

EXAMPLE 1

An emulsion is prepared from the following ingredients:

| Component | Grams |
| --- | --- |
| Part A | |
| Water | 79.7 |
| Methylparaben | 0.2 |
| Polysorbate 80 | 2.0 |
| Part B | |
| White beeswax | 12.0 |
| Glyceryl monostearate | 4.0 |
| Polysorbate 65 | 2.0 |
| Propylparaben | 0.1 |

To produce the emulsion, the components of Part A are mixed and heated to temperatures above about 93° C. (200° F.), but below the boiling point, with thorough stirring. The components of Part B are mixed and heated to similar temperatures, with stirring. Part A is agitated with a high shear mixer while Part B is added. Stirring is reduced to a moderate level, the emulsion is allowed to cool to temperatures less than about 43° C. (110° F.) and sufficient additional water is added to provide a total emulsion weight of 100 grams.

This emulsion is found to be storage stable at room temperatures without significant visible phase separation for at least three months. When phase separation does occur, the emulsion can still be used to coat particles for a few days following a brief moderate agitation to recombine the phases. As produced, the emulsion has a viscosity about 400 centipoise (as measured by a Brookfield rotating viscometer, using a No. 4 spindle at 30 r.p.m.), and a pH about 7.2.

EXAMPLE 2

Using the procedure of the preceding example, an emulsion is prepared from the following components:

| Component | Grams |
|---|---|
| Part A | |
| Water | 80.0 |
| Polysorbate 80 | 2.0 |
| Part B | |
| Carnauba wax | 8.0 |
| White beeswax | 6.0 |
| Glyceryl monostearate | 2.0 |
| Polysorbate 65 | 2.0 |

The emulsion shows visible phase separation after standing overnight, but can be redispersed with moderate agitation for use to coat particles.

EXAMPLE 3

Sugar coated chewing gum pieces are coated with wax and polished, using the following procedure. A batch of about 125,000 gum base pieces, weighing about 925 milligrams each, are coated with about 150 kilograms of sugar syrup in an unlined metal rotating pan having a diameter about 150 centimeters, using conventional techniques. The coated pieces are allowed to dry, without removal from the pan, and are then sprayed with about 250 grams of the wax emulsion of preceding Example 1 to moisten the particle surfaces. About 90 grams of powdered carnauba wax are dusted over the surface of the moist particles, and pan rotation is continued without introduction of air streams for about 30 minutes to produce a high gloss coating. The particles are transferred to drying trays and allowed to stand at room temperature for at least eight hours, before imprinting with identification markings.

EXAMPLE 4

A 42.5 kilogram portion of sugar coated tablets, numbering approximately 100,000, is placed in a rotating unlined pan having a diameter about 75 centimeters. A syrup is prepared by mixing 3.21 kilograms of sugar and 1.07 kilograms of water and heating to about 75° C. with stirring. About 250 milliliters of the syrup are reserved for a final coating. The remaining syrup is cooled to about 70° C. and 15.7 grams of gelatin and 184.4 grams of additional sugar are added, with mixing; after further cooling to about 50° C., 540 grams of D&C Red No. 7 dye are added and the specific gravity is adjusted to about 38° Baumé with water to prepare a coloring agent. The coloring agent is applied in fifteen separate light spray coats. The reserved initial syrup is adjusted to about 34° Baumé at about 35° C. and is sprayed onto the colored tablets as a final sugar coating.

After about 25 minutes of drying in the pan, about 140 grams of the emulsion of preceding Example 1 are sprayed onto the particles, 40 grams of powdered carnauba wax are dusted over the moist tablets, and rotation is continued until a high gloss is obtained. The tablets are removed from the pan, allowed to air dry for at least eight hours, and are imprinted with identifying marks.

The invention has been described with reference to specific embodiments and examples, which are not intended to limit the scope of the invention as it is defined by the appended claims.

What is claimed is:

1. A process for providing a wax coating to particles which contain or are coated with sugar, comprising: (a) applying to the particles an emulsion coating having a wax-containing internal phase and an aqueous external phase, and which is substantially free of sugars; (b) without drain the particles, applying a powdered wax coating to the emulsion-coated particles; (c) tumbling the particles to polish the wax coating; and (d) drying the polished particles.

2. The process of claim 1, wherein more than one wax comprises the internal phase of the emulsion.

3. The process of claim 1, wherein the emulsion is formed by combining molten wax and an aqueous material.

4. The process of claim 3, wherein the emulsion further has a surfactant as a component.

5. The process of claim 3, wherein the emulsion further has a biocide as a component.

6. The process of claim 1, wherein the emulsion comprises beeswax.

7. The process of claim 1, wherein the emulsion comprises carnauba wax.

8. The process of claim 1, wherein the emulsion comprises both beeswax and carnauba wax.

9. The process of claim 1 which is conducted with sugar-coated particles.

10. The process of claim 1 which is conducted in the same equipment used for sugar coating, without removal of particles following a sugar coating procedure.

11. The process of claim 1, which is conducted with the substantial absence of volatile organic solvents.

12. The process of claim 1, wherein the particles are tablets.

13. The process of claim 1, wherein the particles are chewing gum.

14. A process for providing a polished wax coating to particles, comprising:
   (a) placing the particles in an inclined rotating pan;
   (b) applying a sugar coating to the particles by spraying thereon a sugar syrup, as the pan rotates;
   (c) without removing the particles from the pan, applying as the pan rotates an aqueous-continuous emulsion having wax in the internal phase, the emulsion being substantially free of sugars;
   (d) without drying the particles, and without removing the particles from the pan, applying a powdered wax coating to the emulsion-coated particles;
   (e) without removing the particles from the pan, rotating the pan to cause tumbling of the powder-coated particles to polish the wax; and
   (f) drying the polished particles.

15. The process of claim 14, wherein the wax of the emulsion comprises beeswax.

16. The process of claim 14, wherein the powdered wax comprises carnauba wax.

* * * * *